United States Patent [19]

Oblas et al.

[11] Patent Number: 5,027,650
[45] Date of Patent: Jul. 2, 1991

[54] METHOD FOR CHARACTERIZATION OF ADHESION BETWEEN HARD MATERIALS

[75] Inventors: Daniel W. Oblas, Bedford; Vinod K. Sarin, Lexington, both of Mass.; Jaime Sanchez, Medellin, Colombia; Frank E. Sivo, Reading, Mass.

[73] Assignee: GTE Laboratories Incorporated, Waltham, Mass.

[21] Appl. No.: 520,415

[22] Filed: May 8, 1990

[51] Int. Cl.$^5$ ............................................. G01N 19/04
[52] U.S. Cl. ...................................... 73/150 A; 73/78
[58] Field of Search ................... 73/150 A, 150 R, 78

[56] References Cited

U.S. PATENT DOCUMENTS

| | | | |
|---|---|---|---|
| 2,801,540 | 8/1957 | Rondeau | 73/150 A |
| 4,892,792 | 6/1990 | Sarin et al. | 428/698 |
| 4,899,581 | 2/1990 | Allen et al. | 73/150 A |
| 4,950,558 | 8/1990 | Sarin | |

OTHER PUBLICATIONS

J. Valli, "A Review of Adhesion Test Methods", *J. Vac. Sci. Technol. A* 4 (6), Nov./Dec. 1986, 3007-3014.
T. Arai et al., "Evaluation of Adhesion Strength of Thin Hard Coatings", *Thin Solid Films,* 154 (1987) 387-401.
A. Kinbara et al., "Adhesion Measurement of Non-M-etallic Thin Films Using a Scratch Method", *Thin Solid Films,* 163 (1988), 67-73.

*Primary Examiner*—Daniel M. Yasich
*Attorney, Agent, or Firm*—Frances P. Craig

[57] ABSTRACT

A microscratch-test method for measuring adhesion between a first material and a second material adhered to one another at an interface and forming an article. The method involves polishing a planar surface of the article generally normal to the interface and exposing the interface and the first and second materials. A static load of predetermined mass is applied to a starting point on the first or second material in a direction generally normal to the planar surface, using a load means of a third material harder than the first and second materials. The load means is moved across the planar surface from the starting point in a straight line generally toward and across the interface at an angle relative to the interface of between 90° and about 20°. These steps are repeated, varying the mass. The starting point for each repetition is spaced apart from other starting points but is approximately equidistant with other starting points from the interface. The lowest value of the predetermined mass is observed at which a predetermined level of damage to one or more of the interface, first material, and second material occurs. The scratch angle may be constant or may vary with each repetition.

3 Claims, 5 Drawing Sheets

METHOD FOR CHARACTERIZATION OF ADHESION BETWEEN HARD MATERIALS

BACKGROUND OF THE INVENTION

This invention relates to a method for characterizing the adhesion of hard materials to one another, and in particular to a method for physically stressing the materials in the region of the interface between the materials to aid in such characterization.

In recent years, considerable research has been devoted to the application of hard, thin coatings to hard materials by chemical or physical vapor deposition processes. Such coatings are applied to enhance the chemical and physical properties of the substrate materials. The goal of such research is to optimize the coating/substrate design to achieve maximum reduction of factors inducing failure of the substrate in use. Typical of such factors are abrasive wear, chemical wear, and thermal degradation. Examples of such optimized coating/substrate design are described in U.S. Pat. Nos. 4,965,140, 4,950,588, and 4,988,564, all commonly assigned herewith and incorporated herein by reference. Further examples are described in U.S. Pat. No. 4,892,792 (entitled "AlN Coated Silicon Nitride-Based Cutting Tools"), also commonly assigned herewith and incorporated herein by reference.

In order to facilitate optimization of the properties of a coating/substrate composite article, the characteristics of potential substrate and coating materials and their interaction must be understood, particularly their behavior in the service environment. Based on such understanding, maximally compatible materials may be selected for a given use. Many of such properties are known, or may be calculated or speculated and empirically verified. Although the interfacial strength, or adhesion (adherence), of materials in such composite articles is a critical factor in the selection of compatible materials, this factor has remained difficult to quantify and is poorly understood. Adhesion has been defined as the amount of energy required to separate a coating from its substrate.

Adhesion is a macroscopic property influenced by many factors, including interdiffusion of materials across the interface between the substrate and the coating, compound formation at the interface, coating and substrate morphologies, defect structures, and residual stresses. Such residual stresses are due to deposition procedures or to differences in material properties, e.g. thermal mismatch between the substrate and the coating. Absolute determination of these factors, their interdependence, and the resulting influence on the mechanical properties of the interfacial region is the subject of ongoing research. Without adequate quantification of these parameters, accurate theoretical prediction of coating adherence is impossible. Presently, determination of adherence must be approached empirically through mechanical testing.

Various techniques have been used in attempts to quantify the adherence between coatings and substrates, for example the well known peel test, pull test, indentation test, scratch test (using the Revetest ® apparatus), and thermal shock-laser test, as well as many others. These tests are only partly successful at best, and apply to only a narrow field of materials.

The scratch test is the most widely used adherence test for hard, thin coatings. In this test, a statically loaded, generally conical, diamond tipped indenter is drawn across the surface of the coating as the load is increased, until coating failure is induced. Since the force of the load in this test is applied in a direction normal to the coating surface, the coating, substrate, and interface all are increasingly deformed as the load is increased. Thus when failure occurs, it is difficult to determine the exact point, i.e. in the coating, within the substrate, or at the interface, at which the failure was initiated. Because of the degree of deformation of the coating, substrate, and interface, this prior art scratch test has proved to be less a measure of the adherence of the coating than of the durability of the coated material.

It clearly would be desirable, in order to promote further scientific development and engineering improvements of coated material systems, to have available a technique which is more sensitive to the pure adhesive and cohesive forces between various coatings and substrates. The present invention addresses this need.

SUMMARY OF THE INVENTION

The invention is a method for measuring adhesion between a first material and a second material adhered to one another at an interface and forming an article. The method involves polishing a planar surface of the article, where the planar surface is generally normal to the interface and exposes a portion of each of the interface and the first and second materials. A static load of predetermined mass is applied to a starting point on the first or second material in a direction generally normal to the planar surface. The load is applied by way of a load means of a third material of greater hardness than the first and second materials. The statically loaded load means is moved across the planar surface from the starting point in a straight line generally toward and across the interface at an angle relative to the interface of between 90° and about 20°. The applying and moving steps are repeated, the preselected mass being varied with each repetition. The starting point is varied with each repetition to be spaced apart from other starting points but approximately equidistant with other starting points from the interface. The lowest value of the predetermined mass is observed at which a predetermined level of damage to one or more of the interface, first material, and second material occurs. In narrower aspects of the invention, the angle relative to the interface at which the load means is moved may be constant or may vary with each repetition.

BRIEF DESCRIPTION OF THE DRAWINGS

For a better understanding of the present invention, together with other objects, advantages and capabilities thereof, reference is made to the following Description and appended Claims, together with the Drawings, in which:

FIGS. 5a–5c and 6–9 are photomicrographs representing failure induced in various materials by embodiments of the method according to the invention.

DETAILED DESCRIPTION OF THE PREFERRED EMBODIMENTS

Figure 1:
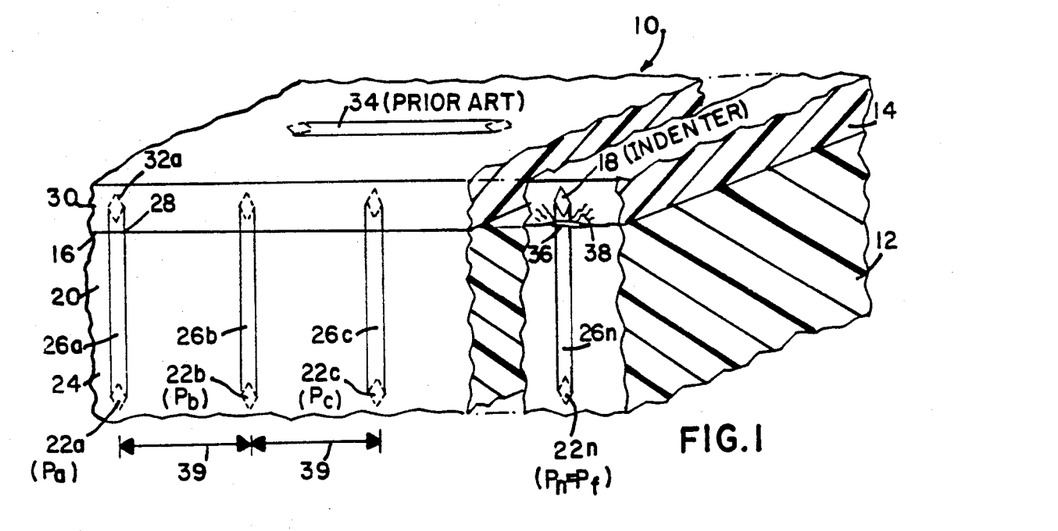
FIG. 1 is a schematic representation of embodiments of a prior art method and the method according to the invention.

The invention described herein presents to the art a needed alternative to the prior art scratch test described above. The Revetest scratch test requires applying a load normal to the surface of the coating and moving the load along the coating surface, as shown in FIG. 1. The method according to the present invention applies a static load normal to a cross-section of the material and generally parallel to the interface. The direction of motion of the scratch inscribed by the statically loaded indenter in the present invention is across the interface on this cross-sectional surface.

The following description of the operation of an exemplary process according to the invention is presented to enable those skilled in the art to more clearly understand and practice the present invention. This description should not be considered as limiting to the scope of the present invention, but merely as illustrative and representative thereof.

FIG. 1 illustrates article 10 including substrate 12 with coating 14 deposited thereon and contacting substrate 12 at interface 16. The load means, diamond indenter 18 statically loaded with static load of predetermined mass $P_a$ is rested on polished surface 20 at starting point 22a on substrate portion 24 of surface 20. Statically loaded indenter 18 is then drawn across surface 20 at constant load $P_a$ along straight path 26a toward and across interface 16 at point 28 and across coating portion 30 of surface 20. Typically, because of the thinness of coating 14, path 26a completely crosses coating portion 28, but may end within coating portion 28 at end point 32a, as shown in FIG. 1.

This configuration produces different stresses within article 10 than does the prior art scratch test, shown at 34 in FIG. 1. The preferred indenter for performing the inventive method is the diamond indenter of the geometry known in the art as Knoop geometry, although other geometries are within the scope of the invention. This is also the geometry used in the prior art Revetest scratch test, but is applied to a different portion of the article and at a constant load for each scratch.

The mechanics involved in deforming a brittle material include elastic deformation, plastic deformation, and crack formation. The load on the indenter produces sub-surface hydro-static, elastic, and plastic deformation zones. Due to the deformation in the plastic zone high strain and shear forces are produced at interface 16. As a result of the induced stress and the brittle material's inability to absorb the energy transmitted, cracks nucleate and grow at or near interface 16.

Figure 2A:
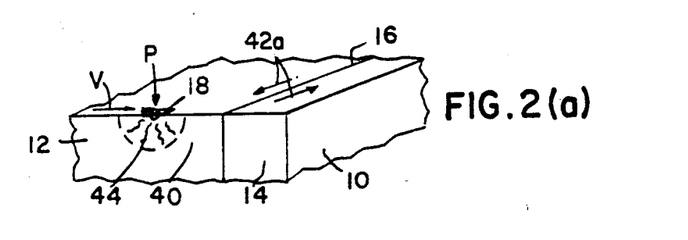
FIGS. 2a-2c show a schematic representation of various stress mechanisms occurring in a sample being tested by an embodiment of the method according to the invention.
Figure 2B:
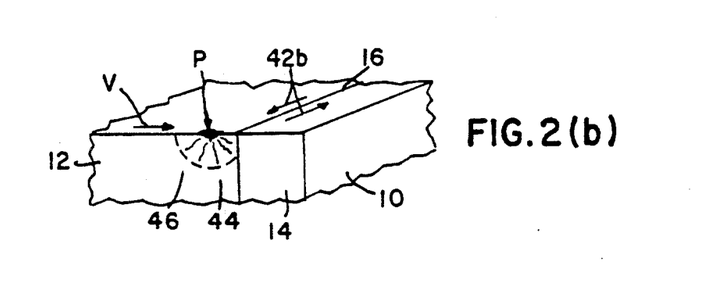
Figure 2C:
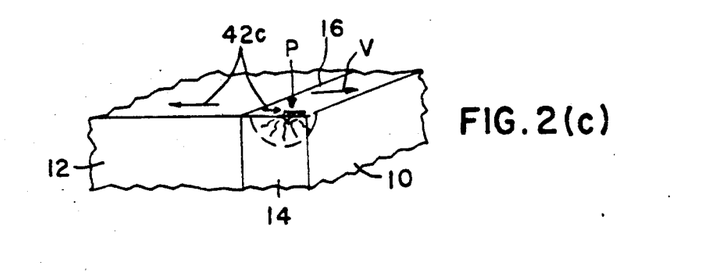

These deformation and crack growth processes are further manifested in the micro-scratch procedure as the deformation area is displaced along the scratch track. During the execution of the test, cracks at and near the interface may be generated by several different mechanisms, as shown in FIG. 2. First, as the indentor approaches the interface it is preceeded by a wave of elastic strain field energy, e.g. at 40 in FIG. 2(a). Shear stresses $42a$ associated with strain field 40 could cause cracking if the fracture strength of the interface is exceeded. Secondly, plastic deformation zone 44, which contains microscopic cracks 46 continually nucleating and growing ahead of indentor 18, impinges on interface 16, as shown in FIG. 2(b). At the interface, applied stresses $42b$ in conjunction with stress concentrators present could cause a crack to form and propogate through the material with the lowest fracture toughness (usually the interface). Finally, the tip of indentor 18 crosses interface 16, as shown in FIG. 2(c). Indentor 18 acts as a plow tearing through the interface 16 and coating 14. The force of indentor 18 could induce normal stresses $42c$ large enough to cause fracture in the interfacial region.

Typically the initial load, $P_a$ (FIG. 1), is selected to be small enough to be unlikely to induce failure in coating 14. The test is repeated a second time, third time, etc. to the $n^{th}$ repeat, as shown in FIG. 1., increasing the mass of the static loading with each repetition from $P_a$ to $P_b$, $P_c$, etc. up to $P_n = P_f$ (FIG. 1), $P_f$ being the lowest mass static load at which the coating fails. Failure of the coating is defined as optically (e.g. microscopically) visible cracking at the interface, shown at 36 in FIG. 1, or optically visible cracking in the coating near the interface, shown at 38 in FIG. 1. Each successive scratch starting point, as $P_b$, $P_c$ in FIG. 1, is approximately the same distance from interface 16 and is spaced apart from prior starting points, as $P_a$, $P_b$, respectively, a sufficient distance 39 to avoid restressing portions of article 10 affected by prior scratches. The paths, as 26b, 26c, 26n, of successive scratches preferably are parallel to path 26a.

The paths of the scratches shown in FIG. 1 are normal to the interface and proceed from the substrate, across the interface, and into the coating, stressing the coating in a tensile mode at a 90° angle to the interface. Other test modes, however, are also within the scope of the invention. For example, the angle formed by the scratch paths with the interface may vary from 90° to about 20°. Also the direction of approach of the scratch path to the interface may be either from the substrate side or from the coating side of the article.

Typically the tested article is a coated cutting tool or a coated structural or wear part, having a substrate of a hard refractory metal or ceramic material. Examples of such substrate materials are tool steels; cemented metal carbides or nitrides; oxides such as alumina or silica, carbides or nitrides of silicon or boron, or of metals such as titanium or aluminum; borides such as titanium diboride; or other suitable refractory materials. The substrates may be monolithic materials, or may be composite materials such as whisker reinforced composites. The coatings applied to such cutting tools or structural or wear parts are selected to impart to the substrates such improved characteristics as wear and chemical resistance, reduced friction, increased fracture toughness or hardness, etc., and may be selected from among the above materials or other suitable refractory materials. Typically, a coating of from 0.5 to about 20 $\mu$m thick is deposited by chemical vapor deposition (CVD), plasma spraying, or physical vapor deposition (PVD) on the substrate, although the inventive method is not limited to such thicknesses or deposition processes.

Other articles and hard materials are within the scope of the invention, for example semiconductor structures of such materials as silicon with such coatings as gallium arsenide, or refractory whiskers or fibers coated with refractory materials. The invention also is useful for characterizing substrate/coating adhesive strength in articles having single-layer coatings or substrate/coating and/or coating/coating adhesive strength in articles having multiple-layer coatings. Of particular interest is the utilization of this novel method to characterize the interfacial adhesion strength in composite materials between the matrix and the reinforcing dispersoids, whether in fiber, whisker, or particulate form. Typically in this mode the dispersoid is treated as a substrate, the matrix as a coating, and any true coating on the dispersoid as a coating layer intermediate the dispersoid and the matrix.

The following Examples are presented to enable those skilled in the art to more clearly understand and practice the present invention. These Examples should not be considered as a limitation upon the scope of the present invention, but merely as being illustrative and representative thereof.

EXAMPLES

Figure 3:
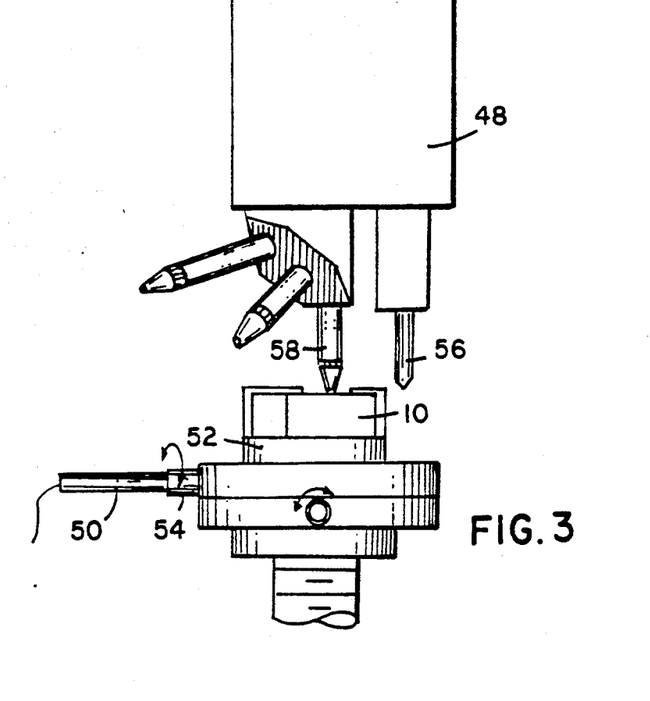
FIG. 3 is a schematic representation of an apparatus useful to perform an embodiment of the method according to the invention.

The apparatus utilized for the Examples below is illustrated in FIG. 3. Microhardness tester apparatus 48, in these Examples a Tukon ® microhardness tester, was utilized to ensure accurate placement and observation of the tests. The stage of the microhardness tester was driven by motor 50 coupled with a controller (not shown), in these Examples an Oriel ® variable speed motor (Encoder Mike ® Model) coupled with an Oriel controller (Model 18008). Motor 50 was capable of driving stage 52 of tester 48 at constant velocity using drive screw type mechanism 54. Preliminary tests were run at various stage velocities between 1 $\mu$m/s and 10 $\mu$m/s, but the observed $L_f$ (load at failure) did not appear to be significantly dependent on stage velocity. Therefore the Examples below all utilize a stage velocity of 5 $\mu$m/s. Also, all of the Examples below utilize diamond indenter 56 having the Knoop geometry.

In these Examples, all samples were prepared by cutting a cross section as shown in FIG. 1, and polishing the cut surface to a sub-micron finish using a 1 $\mu$m diamond paste. Once prepared, the samples were mounted in epoxy and secured to stage 52 (FIG. 3) of microhardness tester 48. The samples were carefully aligned to assure that the indenter would impinge on the polished surface in the desired orientation.

The first scratch was made starting with a small load of 10 g. Observations were made optically at 800× using optical microscopic lens 58 to determine whether or not fracture had occurred. Repeated scratches were made with the load increased in increments of 10 g until fracture was observed. Three more scratches were then run at this load and at a load 5 g smaller to confirm the actual failure load, $L_f$.

Figure 4A:
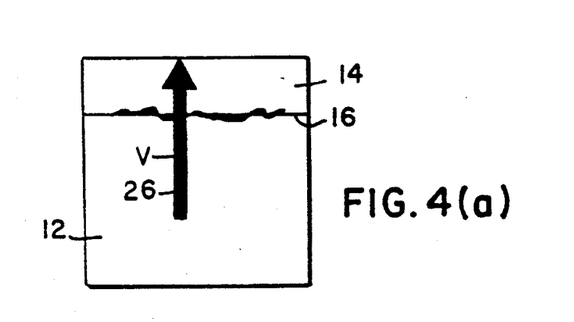
FIGS. 4a–4b show a schematic representation of modes of operation of two embodiments of the method according to the invention.
Figure 4B:
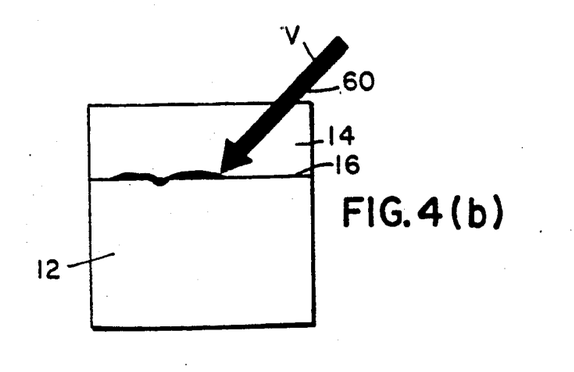

Different test configurations were implemented using this test method. Described below are the tensile and the inclined compressive modes. Schematic representations of these two configurations are shown in FIGS. 4(a) and 4(b) respectively. In the configuration shown in FIG. 4(a) scratch 26 is originated in substrate 12, and is drawn in a direction V perpendicular to interface 16 between substrate 12 and coating 14. Scratch 26 is inscribed across interface 16 and into coating 14. This configuration is termed "tensile mode" because interface 16 is placed in tension as the indenter is drawn across the coating. Scratch 60 of FIG. 4(b), generated in the "inclined compressive mode", originates in the mounting material (not shown) and places interface 16 in compression as the indenter impinges on coating 14. These terms, however, are terms of convenience, since it is adherence at the interface of two materials which is being evaluated, and the difference between substrate and coating for this purpose generally may be ignored. The scratch paths described below are either normal to the interface, as shown in FIG. 4(a), or inclined, as shown in FIG. 4(b), at an angle of up to 70° from the perpendicular (20° from the interface) to induce shear along the coating/substrate interface.

EXAMPLE 1

Figure 5A:
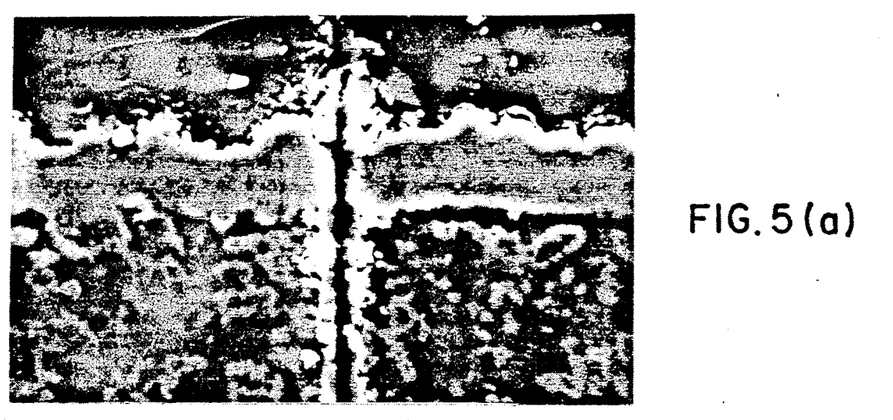
Figure 5B:
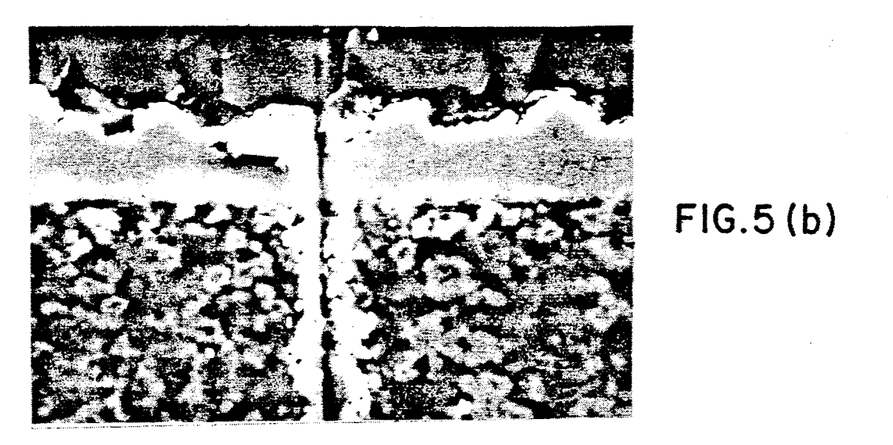

Adhesion of a CVD titanium carbide coating 5 $\mu$m thick on a silicon nitride-based composite substrate was tested in tensile mode as described above. The substrate material included a matrix of silicon nitride grains and an intergranular glassy phase formed from alumina and yttria densification aids. Dispersed in the matrix was about 40% by weight, based on the weight of the matrix, of titanium carbide grains. The results are illustrated in FIG. 5, showing scratches induced in tensile mode about 15 mm apart at loadings of 10 g (FIG. 5(a)), 20 g (FIG. 5(b)), and 15 g (FIG. 5(c)). Examination with an optical microscope showed that at the 10 g loading no failure was observed, but at 20 g loading failure had occurred. A third scratch was then made at 15 g loading, and was observed to have induced failure at the interface. Thus the coating is characterized as failing in tensile mode at a 15 g loading.

EXAMPLE 2

Other materials were tested in tensile mode as described above, and also tested by the prior art method using the Revetest apparatus. The results are shown in Table I, below.

TABLE I

| Samples (Coating/Substrate) | Coating Thickness, $\mu$m | Revetest Results, g | $L_f$ |
|---|---|---|---|
| CVD Samples | | | |
| TiC/SNA-Ce-HfC[a] | 3.20 | — | 15 |
| | 3.50 | — | 15 |
| | 4.70 | — | 30 |
| | 4.70 | — | 25 |
| TiC/SNAT[b] | | | |
| 5% TiC | 4.40 | 26 | 25 |
| 10% TiC | 3.90 | 22 | 20 |
| | 5.00 | — | 20 |
| 15% TiC | 3.00 | — | 10 |
| | 4.30 | 29 | 30 |
| 20% TiC | 10.00 | — | 40 |
| TiC/SNAT[b] | | | |
| 5% TiC | 4.00 | 17 | 20 |
| 10% TiC | 4.00 | 21 | 20 |
| 15% TiC | 4.60 | 19 | 25 |
| 20% TiC | 4.20 | 30 | 25 |
| TiC/VC830[c] | 4.50 | 47–51 | 40 |
| | 4.70 | 49–55 | 40 |
| | 5.00 | 57–61 | 40 |
| | 5.00 | 59–71 | 40 |
| | 7.30 | 73–87 | 50 |
| | 11.00 | 57–71 | 80 |
| TiC/830[c] | 4.30 | — | 50 |
| | 4.50 | — | 55 |
| PVD Samples | | | |
| TiC/VC833[c] | 2.50 | — | 10 |
| | 4.70 | — | 25 |
| | 9.60 | — | 60 |

[a]SNA-Ce-HfC = Si_N_/Al_O_/Ce_O_, with HfC particles.
[b]SNAT = Si_N_/Al_O_ with TiC particles in w/o listed (based on matrix weight).
[c]VC 830, 830, and VC833 = various formulations of Co-cemented WC with TiC and TaC additions.

Figure 6:
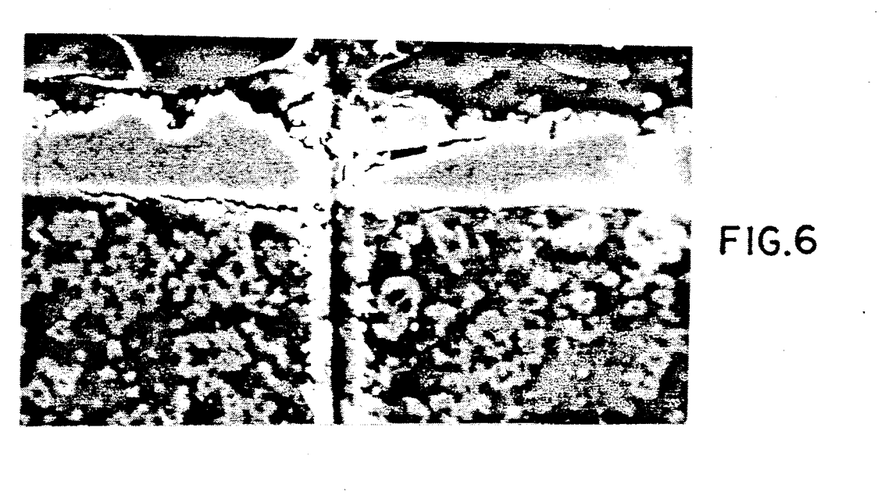

FIG. 6 illustrates an example of failure observed in CVD carbide coatings on ceramic substrates when tested in the tensile mode. In the sample shown in FIG. 6, a titanium carbide coating on a silicon nitride-based titanium carbide dispersoid-containing composite substrate failed in tensile mode at 20 g loading, showing separation at the interface.

Adhesion is known to be greatly affected by coating characteristics resulting from deposition parameters. For example, stress and morphological discontinuities may vary along the periphery of the coated sample. Since the width of the scratches produced by this method is small (about 15 $\mu$m) some of the scratches may be placed at locations of interest along the interface. In this way, materials may be tested at several discrete locations, generating results which are more sensitive to localized influences.

EXAMPLE 3

Figure 7:
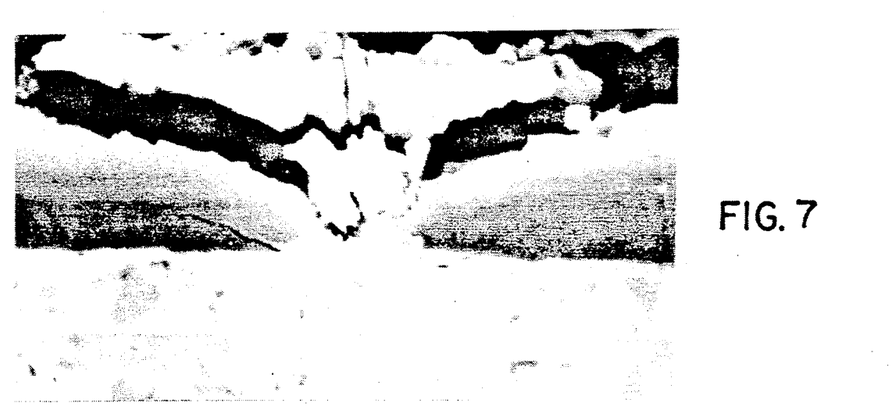

CVD carbide-coated/carbide substrate samples were also prepared and tested as described above. FIG. 7 illustrates a typical failure in a Co-cemented WC sample coated with TiC by CVD.

EXAMPLE 4

Ceramic coating/ceramic substrate samples were prepared by CVD and tested as described above. The samples included aluminum nitride coated silicon carbide and silicon nitride substrates. The results are illustrated in Table II, below.

TABLE II

| Samples (Coating/ Substrate) | Coating Thickness, $\mu$m | Revetest Results, g | $L_f$ |
|---|---|---|---|
| AlN/SSC[a] | 7.80 | 50–65 | 90 |
|  | 4.70 | 50–65 | 90 |
| AlN/RBSN[b] | 5.00 | 75 | 35 |
| AlN/PY6[c] | 10.00 | 70–80 | 40 |
|  | 18.00 | 70–80 | 90 |
| AlN/AY6[d] | 6.50 | >100 | 35 |
|  | 10.00 | >100 | 70 |
|  | 10.00 | >100 | 80 |
|  | 14.00 | >100 | 130 |
|  | 14.00 | >100 | 140 |
|  | 15.70 | 52–58 | 120 |
|  | 22.30 | 56–70 | 140 |
|  | 23.00 | >100 | 195 |
| AlN/SNT[e] | 10.00 | 85 | 70 |
|  | 6.00 | 80 | 50 |
| AlN/SNAT[f] | 10.00 | 65 | 80 |

[a] SSC = Sintered SiC.
[b] RBSN = Reaction bonded Si_N_.
[c] PY6 = Si_N_ with 6 w/o (weight %) Y.
[d] AY6 = Si_N_ with _2 w/o Al_O_ and 6 w/o Y.
[e] SNT = AY6 with 40 w/o TiC particles (based on matrix weight).
[f] SNAT = Si_N_/Al_O_ with TiC particles.

Figure 8:
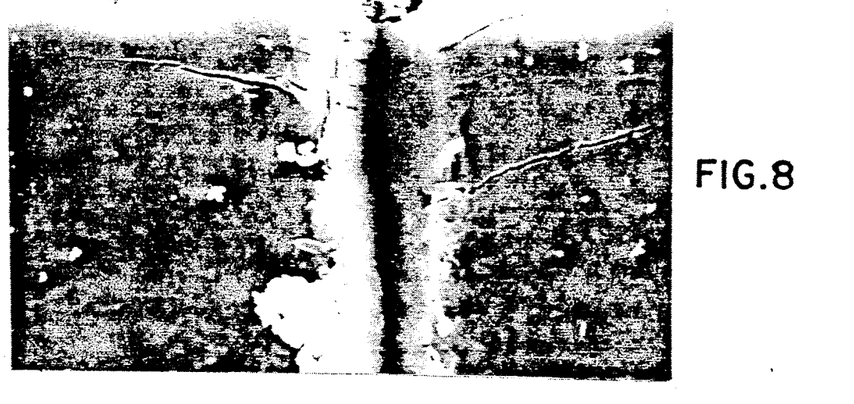

The samples listed in Table II exhibited the greatest resistance to coating-substrate separation. The applied loads necessary to induce cracking were considerably higher than the loads necessary in previous tests. It is believed that the combination of ceramic materials results in the formation of interfacial compounds which strongly anchor the coating to the substrate. FIG. 8 illustrates failure in a typical ceramic/ceramic sample, an AlN coating on a silicon nitride-based substrate.

As shown in Examples 1–4, by using this novel method in the tensile mode, adherence of the coating can be evaluated quantitatively by measurement of the load required to cause failure. Visual observation of the location and type of the crack may also provide insight into the mechanism of failure between various materials.

In actual service, coated materials experience biaxial loading. One component of force compresses the coating surface, while the other component of force acts parallel to the interface creating shear forces between the coating and the substrate. This situation was duplicated experimentally so that the critical shear force causing interfacial cracking could be calculated to quantify adherence. This was accomplished by introducing the indentor described above at an angle to the interface of up to 20° in a compressive mode, as described above. If desired, the angle of impingement may be varied as well as the load. Data obtained from tests in this mode can include load at failure, angle between scratch track and interface at failure, and resolved components of applied load along the shear and axial directions.

EXAMPLE 5

Figure 9:
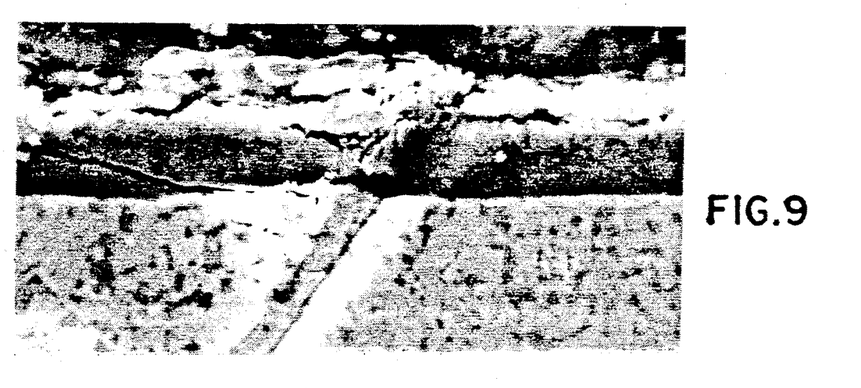

Various coated samples were tested in inclined compressive mode as described above. The results are listed in Table III. The failure induced in a Co-cemented WC (WC-Co) substrate coated with TiC is illustrated in FIG. 9.

TABLE III

| Sample (coating/ substrate) | Coating Thickness, $\mu$m | Revetest Results, g | Angle frm. Interface | $L_f$, g, In. Com. | $L_f$, g, Tens. |
|---|---|---|---|---|---|
| AlN/SSC[a] | 7.80 | 50–65 | 45° | 85 | 90 |
|  | 4.70 |  | 45° | 70 |  |
| AlN/RBSN[b] | 5.00 | 75 | 45° | 40 | 35 |
| AlN/PY6[c] | 10.00 | 70–80 | 52° | 90 | 40 |
| AlN/AY6[d] | 8.00 | >100 | 50° | 130 | 35 |
|  | 11.00 | >100 | 47° | 155 | 195 |
|  | 17.40 | >100 | 52° | 200 | 70 |
|  | 38.50 | >100 | 52° | 100 | 130 |
| AlN/SNT[e] | 10.00 | 85 | 55° | 100 | 70 |
| AlN/SNT[f] | 6.00 | 80 | 45° | 50 | 50 |
| AlN/SNAT[g] | 10.00 | 65 | 55° | 200 | 80 |
| TiC/SNA-Ce-HfC[h] | 3.20 | — | 46° | 15 | 15 |
|  | 3.50 | — | 46° | 20 | 15 |
|  | 4.70 | — | 47° | 25 | 25 |
|  | 4.70 | — | 50° | 25 | 30 |
| TiC/SNAT[g] |  |  |  |  |  |

TABLE III-continued

| Sample (coating/substrate) | Coating Thickness, μm | Revetest Results, g | Angle frm. Interface | $L_f$, g, In. Com. | $L_f$, g, Tens. |
|---|---|---|---|---|---|
| 5% A[i] | 4.00 | 17 | 45° | 30 | 20 |
| 10% A | 4.00 | 21 | 46° | 30 | 20 |
| 15% A | 4.60 | 19 | 45° | 30 | 25 |
| 20% A | 4.20 | 30 | 43° | 35 | 25 |
| TiC/VC830[j] | 5.00 | 59 ± 2 | 55° | 100 | 40 |
|  | 11.00 | 64 ± 7 | 55° | 190 | 80 |

[a] SSC = Sintered SiC.
[b] RBSN = Reaction bonded $Si_xN_y$.
[c] PY6 = $Si_xN_y$ with 6 w/o (weight %) Y.
[d] AY6 = $Si_xN_y$ with 2 w/o $Al_xO_y$ and 6 w/o Y.
[e] SNT = HIPed AY6 with 40 w/o TiC particles (based on matrix weight).
[f] SNT = Hot pressed AY6 with 40 w/o TiC particles (based on matrix weight).
[g] SNAT = $Si_xN_y/Al_xO_y$ with TiC particles.
[h] SNA-Ce-HfC = $Si_xN_y/Al_xO_y/Ce_xO_y$, with HfC particles.
[i] % = weight %
[j] VC830 = various formulations of Co-cemented WC with TiC and TaC additions.

EXAMPLE 6

Co-cemented WC cutting tool substrates with 11 μm TiC coatings were processed under various conditions and tested in tensile mode. The machining performance of these samples was then tested by machining 4340 steel at 700 surface feet/min and 0.050 depth of cut. The results are listed in Table IV below.

TABLE IV

| Sample | Revetest Results, g | $L_f$, g | Flank Wear, in | Crater Wear, in | Nose Wear, in |
|---|---|---|---|---|---|
| A | 65 ± 6 | 80 | 0.0060 | 0.0070 | 0.0120 |
| B | 63 ± 7 | 110 | 0.0060 | 0.0050 | 0.0110 |
| C | 70 ± 5 | 110 | 0.0055 | 0.0045 | 0.0085 |
| D | 77 ± 8 | 120 | 0.0055 | 0.0040 | 0.0085 |
| E | 68 ± 5 | 100 | 0.0055 | 0.0050 | 0.0130 |

Table IV indicates that there is substantially reduced wear in the samples in which this novel scratch test indicate improved adhesion between the coating and the substrate.

The method according to the present invention permits a more independent analysis of the effect of deformation under load on each of the substrate, the coating, and the interface than prior art methods. The method is directed more precisely to the analysis of the pure adhesive and cohesive forces between various coatings and substrates than prior art methods. Additionally, the method is straightforward, and can be performed utilizing a simple combination of readily available apparatus. Further, the method may be utilized on a greater variety of composite articles such as those described above. The method is particularly useful as an analysis tool to aid in the development of custom-engineered interfaces to enhance adhesion and component performance.

While there has been shown and described what are at present considered the preferred embodiments of the invention, it will be obvious to those skilled in the art that various changes and modifications can be made therein without departing from the scope of the invention as defined by the appended Claims.

We claim:

1. A method for measuring adhesion between a first material and a second material adhered to one another at an interface and forming an article, said method comprising the steps of:

polishing a planar surface of said article, wherein said planar surface is generally normal to said interface and exposes a portion of each of said interface and said first and second materials;

applying a static load of predetermined mass to a starting point on said first or second material in a direction generally normal to said planar surface, wherein said load is applied by way of a load means formed of a third material of greater hardness than said first and second materials;

moving said statically loaded load means across said planar surface from said starting point in a straight line generally toward and across said interface at an angle relative to said interface between 90° and about 20°;

repeating said applying and said moving steps, wherein said preselected mass is varied with each said repetition, said starting point is varied with each repetition to be spaced apart from others of said starting points but approximately equidistant with others of said starting points from said interface; and observing the lowest value of said predetermined mass at which a predetermined level of damage to one or more of said interface, said first material, and second material occurs.

2. A method in accordance with claim 1 wherein said angle relative to said interface is the same for each said repetition of said applying and said moving steps.

3. A method in accordance with claim 1 wherein said angle relative to said interface is varied for each said repetition of said applying and said moving steps, and the observing step further includes observing the greatest value of said angle at which a predetermined level of damage to one of said interface, said first material, and said second material occurs.

* * * * *